United States Patent
Becwar et al.

(10) Patent No.: US 6,682,931 B2
(45) Date of Patent: *Jan. 27, 2004

(54) RECOVERING CRYOPRESERVED CONIFER EMBRYOGENIC CULTURES

(75) Inventors: Michael Ryan Becwar, Summerville, SC (US); Sharon Anne Krueger, Summerville, SC (US)

(73) Assignee: MeadWestvaco Corporation, Stamford, CT (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 96 days.

(21) Appl. No.: 09/573,160

(22) Filed: May 19, 2000

(65) Prior Publication Data

US 2002/0192818 A1 Dec. 19, 2002

Related U.S. Application Data

(60) Provisional application No. 60/136,000, filed on May 25, 1999.

(51) Int. Cl.$^7$ ................................................. C12N 5/00
(52) U.S. Cl. ........................ 435/422; 435/420; 435/431; 435/1.1; 435/1.3; 436/18
(58) Field of Search ................................ 435/422, 420, 435/431, 1.1, 1.3; 436/18

(56) References Cited

U.S. PATENT DOCUMENTS

| | | |
|---|---|---|
| 4,957,866 A | 9/1990 | Gupta et al. |
| 5,034,326 A | 7/1991 | Pullman et al. |
| 5,036,007 A | 7/1991 | Gupta et al. |
| 5,183,757 A | 2/1993 | Roberts |
| 5,187,092 A | 2/1993 | Uddin |
| 5,236,841 A | 8/1993 | Gupta et al. |
| 5,294,549 A | 3/1994 | Pullman et al. |
| 5,413,930 A | 5/1995 | Becwar et al. |
| 5,491,090 A | 2/1996 | Handley et al. |
| 5,506,136 A | 4/1996 | Becwar et al. |
| 5,677,185 A | 10/1997 | Handley, III |
| 5,731,191 A | 3/1998 | Rutter et al. |
| 5,731,204 A | 3/1998 | Rutter et al. |
| 5,856,191 A | 1/1999 | Handley |
| 5,965,438 A | 10/1999 | Kadkade et al. |

FOREIGN PATENT DOCUMENTS

| | | |
|---|---|---|
| NZ | 504773 | 1/2002 |
| WO | 9600049 | 1/1996 |
| WO | 9637096 | 11/1996 |

OTHER PUBLICATIONS

Hakman, I. and S. von Arnold. Plantlet regeneration through somatic embryogenesis in *Picea abies* (Norway spruce). *Journal of Plant Physiology* 121:149–158, 1985.

Hakman, I.C. and S. von Arnold. Somatic embryogenesis and plant regeneration from suspension cultures of *Picea glauca* (White spruce). *Physiologia Plantarum* 72:579–587, 1988.

Hakman, I., L. C. Fowke, S. von Arnold, and T. Eriksson. The development of somatic embryos in tissue cultures initiated from immature embryos of *Picea abies* (Norway spruce). *Plant Science* 38:53–59, 1985.

Kendall, E.J., K.K. Kartha, J.A. Qureshi, P. Chermak. Cryopreservation of immature spring wheat zygotic embryos using an abscisic acid pretreatment. *Plant Cell Reports* 12:89–94, 1993.

Luo, J. and B. M. Reed. Abscisic acid–responsive protein, bovine serum albumin, and proline pretreatments improve recovery of in vitro currant shoot–tip meristems and callus cryopreserved by vitrification. *Cryobiology* 34:240–250, 1997.

Murashige, T. and F. Skoog. A revised medium for rapid growth and bioassays with tobacco tissue cultures. *Physiologia Plantarum* 15:473–497, 1962.

von Arnold, S. and I. Hakman. Regulation of somatic embryo development in *Picea abies* by abscisic acid (ABA). *Journal of Plant Physiology* 132:164–169, 1988.

Benson, E.E., P. T. Lynch, and G.N. Stacey. Advances in plant cryopreservation technology: current applications in crop plant biotechnology. *CAB International*, 1998.

Gupta, P. K. and D. J. Durzan. Shoot multiplication from mature trees of Douglas–fir (*Pseudotsuga menziesii*) and sugar pine (*Pinus lambertiana*). *Plant Cell Reports* 4:177–179, 1985.

*Primary Examiner*—Leon B. Lankford, Jr.
(74) *Attorney, Agent, or Firm*—Daniel B. Reece, IV; Terry B. McDaniel; Thomas A. Boabinski

(57) ABSTRACT

This invention relates to a method for improving the growth and regeneration potential of embryogenic cell and tissue cultures of coniferous plants retrieved from cryopreservation. In particular, this invention relates to the use of abscisic acid in the post-cryopreservation recovery medium to improve both the growth and somatic embryo production of embryogenic cell and tissue cultures of conifers, thereby enabling more rapid proliferation of the embryogenic cultures and a subsequent increase in the yield of somatic embryos. This method is well-suited for employment with a number of biotechnological uses of embryogenic cultures of coniferous plants retrieved from cryopreservation, including use with embryogenic cultures of coniferous plants and with genetically transformed embryogenic cultures of coniferous plants for producing clonal planting stock useful for reforestation.

34 Claims, No Drawings

RECOVERING CRYOPRESERVED CONIFER EMBRYOGENIC CULTURES

This application claims the benefit of Provisional Application No. 60/136,000 filed May 25, 1999.

FIELD OF INVENTION

This invention relates to a method for improving the growth and regeneration potential of embryogenic cell and tissue cultures of coniferous plants retrieved from cryopreservation. In particular, this invention relates to the use of abscisic acid in the post-cryopreservation recovery medium to improve both the growth and somatic embryo production of embryogenic cell and tissue cultures of conifers, thereby enabling more rapid proliferation of the embryogenic cultures and a subsequent increase in the yield of somatic embryos. This method is well-suited for employment with a number of biotechnological uses of embryogenic cultures of coniferous plants retrieved from cryopreservation, including use with embryogenic cultures of coniferous plants and with genetically transformed embryogenic cultures of coniferous plants for producing clonal planting stock useful for reforestation.

BACKGROUND OF THE INVENTION

Cryopreservation is the storage of living cells at ultra-low (cryogenic) temperatures, usually in liquid nitrogen (−196° C.) or in its vapor phase (about −150° C.). Cryopreservation is the preferred method for long-term storage and "banking" of valuable in vitro biological material used in or derived from biotechnology. At cryogenic temperatures the biological activity of the cells and tissues is halted. The cells and tissues remain viable throughout the cryopreservation process due to the application of various cryoprotective procedures (Benson et al. 1998).

There are several methods of freezing used in cryopreservation of biological materials such as living cells or tissues. The basic method is to rapidly cool the biological material or to directly plunge the material into liquid nitrogen. However, this method only works on tissues which remain viable at low moisture content levels. For example, many temperate zone seeds (such as pine seeds which have been dried to below about 15% water content) can be successfully cryopreserved using this method.

A different cryopreservation method is frequently used where the biological material has a relatively high moisture content or where the material may not tolerate dehydration to a lower moisture level. This method involves first treating the biological material with a cryoprotective chemical or combination of cryoprotective chemicals. The treated material is subsequently cooled to about −40° C., then rapidly cooled (e.g., directly plunged into liquid nitrogen) to cryogenic temperatures. This method is the one most frequently employed for cryopreservation of in vitro derived cells and tissues.

Another well-known cryoprotective method is "vitrification." This method involves the treatment of biological materials with high levels of cryoprotective chemicals in combination with a rapid cooling of the treated materials to cryogenic temperature.

Regardless of the cryogenic freezing method employed, recovery of viable cells after cryopreservation is dependent upon both pre-cryopreservation and post-cryopreservation treatments. In vitro manipulation of the plant tissues or cells in the second and third cryogenic freezing methods noted above are essential to most pre-cryopreservation and post-cryopreservation recovery protocols (Benson et al. 1998). Pre-cryopreservation treatments commonly include the application of a cryoprotective chemical such as glycerol or dimethyl sulfoxide (DMSO). Also, the osmotic potential of the in vitro culture medium is often decreased in the pre-cryopreservation treatment of tissues or cells via the addition of sugars or sugar alcohols such as sucrose, sorbitol, and the like. Post-cryopreservation treatments commonly include the dilution of the cryoprotective chemicals and the osmoticants in the culture medium. Such traditional pre-cryopreservation and post-cryopreservation procedures are commonly practiced and are familiar to those skilled in the art of cryopreservation of plant tissues and cells.

Culture media in which the tissues or cells are grown and proliferated during both the pre-cryopreservation and post-cryopreservation phases typically contain six groups of ingredients: inorganic nutrients, vitamins, organic supplements, a carbon source (i.e., sugars), phytohormones (e.g., auxins or auxins and cytokinins), and a gelling agent for semi-solid or gelled medium. Thus, a commonly used pre-cryopreservation medium for embryogenic cultures would include a standard culture medium (e.g., a medium containing inorganic nutrients, vitamins, organic supplements, and sucrose like that taught by Murashige and Skoog (1962) or a modification thereof) coupled with an auxin, possibly a cytokinin, sorbitol, and DMSO. A typical post-cryopreservation medium for embryogenic cultures would include a standard culture medium, an auxin and possibly a cytokinin, but would be devoid of the cryoprotective chemicals and additional osmotic agents. Frequently, the tissues and cells are initially cultured during post-cryopreservation for a very brief period (typically, one day) on a temporary recovery medium to allow both the cryoprotective chemicals and the additional osmotic agents used in the pre-cryopreservation medium to diffuse out of the tissue and cells. The tissues or cells are then transferred to the same (fresh) medium, lacking cryoprotective chemicals and osmotic agents, to induce recovery and growth. The actively growing tissues or cells can then be utilized for regeneration of plants, or for other biotechnological and genetic engineering purposes.

A significant problem facing those who work with cells and tissue cultures from trees is how to rapidly recover and multiply by proliferation the embryogenic cultures during the post-cryopreservation phase of the somatic embryogenesis process. Somatic embryogenic cultures are employed in the regeneration of trees for clonal propagation, and in the genetic transformation and subsequent regeneration of transgenic trees. It is well-known that embryogenic cultures in general, and pine embryogenic cultures in particular, decline in regeneration potential as the time in culture increases. It is, therefore, important to decrease the length of time taken to multiply or bulk-up the cultures for use in clonal propagation or genetic transformation. It is also believed that increased time in culture may increase the probability of deleterious genetic changes or mutations that result in unwanted somaclonal variation. Such variations are particularly undesirable in clonal propagation and genetic engineering processes. Thus, a central problem or challenge in somatic embryogenesis systems is the need to keep the time in culture to a minimum, while simultaneously producing large amounts of embryogenic tissue or cells which have the potential to produce large numbers of harvestable somatic embryos. This invention addresses the restraints imposed on such systems due to slow growth and recovery during a specific step of the process, namely, the post-cryopreservation recovery phase.

Propagation by somatic embryogenesis refers to methods whereby embryos are produced in vitro from embryogenic cultures. The embryos are referred to as somatic because they are derived from the somatic (vegetative) tissue, rather than from the sexual process. Vegetative propagation via somatic embryogenesis has the capability to capture all genetic gain of highly desirable genotypes. Furthermore, these methods are readily amenable to automation and mechanization. These qualities endow somatic embryogenesis processes with the potential to produce large numbers of individual clones for reforestation purposes.

It was not until 1985 that somatic embryogenesis was discovered in conifers (Hakman et al. 1985) and the first viable plantlets were regenerated from conifer somatic embryos (Hakman and von Arnold 1985). Since 1985, conifer tissue culture workers throughout the world have pursued the development of somatic embryogenesis systems capable of regenerating plants. The goal of much of this work is to develop conifer somatic embryogenesis as an efficient propagation system for producing clonal planting stock en masse. Additionally, the embryogenic system interfaces very well with genetic engineering techniques for production of transgenic clonal planting stock of conifers.

The somatic embryogenesis processes utilized with coniferous plants usually involves seven general steps: 1) culture initiation, 2) culture maintenance, 3) embryo development, 4) embryo maturation, 5) embryo germination, 6) conversion, and 7) field planting. An additional step, cryopreservation, has become an integral component in conifer somatic embryogenesis. Cryopreservation is important because it is necessary to determine the genetic potential of plants regenerated from each culture before clonal planting stock can be produced. This determination of the genetic potential is done in a "clonal field test" which typically takes four to six years to complete. Therefore, cryopreservation of the embryogenic cultures, which are represented in the clonal field test, has become the preferred way for long-term storage during the completion of the clonal field test. While cryopreservation of embryogenic cultures can be practiced throughout the somatic embryogenesis process, it is commonly practiced during the first three general steps noted above; and preferably practiced with newly initiated and/or maintained embryogenic cultures.

The importance of abscisic acid (ABA) during the development and maturation of zygotic embryos is well known, and ABA has been used routinely to stimulate embryo development in somatic embryogenic systems (von Arnold and Hakman, 1988). For example, U.S. Pat. No. 4,957,866 teaches the use of ABA in the embryo development media. Likewise, in U.S. Pat. Nos. 5,034,326 and 5,036,007 the phytohormone ABA along with activated carbon has been reported to be beneficial in the semi-solid development media for various conifers. U.S. Pat. No. 5,294,549 teaches the incorporation of ABA and gibberellic acid into the embryo development media. U.S. Pat. Nos. 5,187,092, 5,183,757, and 5,236,841 teach the use of ABA in the development step in conifer somatic embryogenesis. In each of these methods ABA is added for the purpose of facilitating embryo development.

U.S. Pat. No. 5,856,191 by Handley (1999) employs ABA in both the initiation and maintenance medium for pine embryogenic cultures prior to cryopreservation. The use of ABA in these earlier phases of the pine somatic embryogenesis process differs from the use of ABA in the post-cryopreservation recovery medium taught by the current invention. That is, while U.S. Pat. No. 5,856,191 claims the cryopreservation of pine embryogenic cultures that have been initiated on culture medium containing ABA, the current invention teaches the use of ABA in the post-cryopreservation phase of culture growth and recovery from cryogenic storage. It has been found that the coupling of the present method with the process taught in U.S. Pat. No. 5,856,191 yields a marked improvement in the growth of embryogenic cultures during the critical phase of recovery from cryogenic storage. Indeed, there are clear advantages to using ABA in both the initiation and maintenance phase prior to cryopreservation (as taught in U.S. Pat. No. 5,856,191), and in subsequently employing ABA in the post-cryopreservation phase of culture growth and recovery from cryogenic storage as taught in the current invention.

Heretofore there has been no evidence that the use of ABA in the phase of recovery of embryogenic cells from cryogenic storage, either in plants in general or with coniferous species, would be beneficial. In fact, although it is well known that ABA is important in the development of embryos both in vivo and in vitro, the ability of ABA to stimulate proliferation of embryogenic tissue growth in material emerging from cryogenic storage was unexpected.

ABA has been added to a pre-cryopreservation medium to successfully cryopreserve wheat zygotic embryos (Kendall et al. 1993). However, the effect of ABA to improve the recovery and growth during the post-cryopreservation step was not examined or suggested in this study. The wheat embryos resumed growth when cultured during the post-cryopreservation step on an MS-based medium containing an auxin, but devoid of ABA. While the treatment of currant meristems and callus during the pre-cryopreservation phase with an ABA-responsive protein was shown to improve recovery after a vitrification method of freezing (Luo and Reed 1997), the study did not suggest the use of, or examine the effect of, adding ABA to the post-cryogenic medium to improve recovery and growth. Indeed, we are not aware of any work that teaches the use ABA to improve the growth of embryogenic cultures of plants, including conifers, during the post-cryopreservation step.

Therefore, an object of the present invention is to provide a method for improving the recovery and growth of embryogenic cultures of coniferous plants recovered from long-term or short-term cryopreservation.

A further object of the present invention is to improve the yield of somatic embryos obtained from the proliferating embryogenic cultures of coniferous plants recovered from long-term or short-term cryopreservation.

Another object of the present invention is to decrease the time required to multiply and proliferate the embryogenic cultures of coniferous plants retrieved from cryopreservation.

A further object of the present invention is to provide an improved method for the recovery of embryogenic cultures of the genus Pinus and Pinus interspecies hybrids from cryopreservation so that these cultures can be used to regenerate clonal planting stock via somatic embryogenesis.

Another object of the present invention is to provide an improved method for the recovery of embryogenic cultures of the genus Pinus and Pinus interspecies hybrids which have been genetically engineered to contain at least one transgene from cryopreservation so that these cultures can be used to regenerate transgenic clonal planting stock via somatic embryogenesis.

SUMMARY OF THE INVENTION

The above objectives are achieved by the use of an improved method for recovering embryogenic cultures of coniferous plants from cryopreservation. This method enables the practitioner to increase the growth of embryogenic cell lines retrieved from cryogenic storage, and thus more quickly have large amounts of embryogenic tissue available for subsequent use. In addition, this method enables the practitioner to increase the yield of somatic embryos harvested from the embryogenic cultures recovered from cryopreservation. This was accomplished via the addition of abscisic acid to the post-cryopreservation recovery medium on which the thawed embryogenic culture was placed for growth. The abscisic acid is utilized in combination with standard (traditional) phytohormones employed during the post-cryopreservation recovery phase.

This method is well-suited for use with coniferous embryogenic cultures for producing clonal planting stock useful for reforestation. Likewise, the present method can be employed in conjunction with genetically transformed coniferous embryogenic cultures for producing transgenic clonal planting stock useful for reforestation.

DESCRIPTION OF THE PREFERRED EMBODIMENT

The present invention is a method for recovering living embryogenic cultures of coniferous plants which have been subjected to cryopreservation which comprises: 1) thawing the embryogenic culture, and 2) culturing the thawed embryogenic culture on post-cryopreservation recovery medium containing a sufficient amount of nutrients, a suitable level of gelling agent, abscisic acid, and a sufficient amount of additional phytohormone for a sufficient period of time, under suitable environmental conditions, to recover (i.e., proliferate and multiply) the embryogenic culture.

Where warranted, an additional step may be employed to allow undesired cryoprotective chemicals and/or osmotic agents to diffuse out of the embryogenic cultures. This method for recovering living embryogenic cultures of coniferous plants which have been subjected to cryopreservation comprises: 1) thawing the embryogenic culture, 2) culturing the thawed embryogenic culture on a temporary recovery medium containing a sufficient amount of nutrients, suitable level of gelling agent, and a sufficient amount of phytohormone for a period of time sufficient to lower the concentration of cryoprotective chemicals and osmotic agents contained in the embryogenic culture; and 3) further culturing the thawed embryogenic culture on post-cryopreservation recovery medium containing a sufficient amount of nutrients, a suitable level of gelling agent, abscisic acid and a sufficient amount of additional phytohormone for a sufficient period of time, under suitable environmental conditions, to recover (i.e., proliferate and multiply) the embryogenic culture.

The current method of using ABA in the post-cryopreservation medium can be employed in methods used to regenerate conifers via somatic embryogenesis. Methods to regenerate Pinus and Pinus interspecies hybrids via somatic embryogenesis are taught in U.S. Pat. Nos. 5,491,090; 5,506,136; 5,731,191; 5,731,204; and 5,856,191 (which are hereby incorporated by reference). Likewise, the current method can be employed to regenerate via somatic embryogenesis conifers which have been genetically transformed to contain at least one transgene. Embryogenic cultures recovered via the present method also exhibit improved production and yields of somatic embryos.

The present invention lies in the incorporation of abscisic acid (ABA) into the post-cryopreservation recovery medium of conifer embryogenic cell cultures. A suitable level of ABA for use in this invention is from about 1.0 to about 100.0 milligrams per liter of medium (mg/l) of medium. The preferred ABA level is about 5.0 to about 50.0 mg/l.

While most cell lines exhibit improved growth rates when grown on post-cryopreservation recovery medium containing ABA than when grown on medium which lacks ABA, the degree of improved growth of such embryogenic cultures depends in part upon the cell line employed. It may be possible in the future to better determine the morphological and/or biochemical differences among cell lines which quantify the degree of improved growth-response to ABA in the post-cryopreservation recovery medium.

The present method is suitable for use with embryogenic cultures of coniferous plants. It is preferred to employ the present method with conifers of the genus Pinus and Pinus interspecies hybrids. This method is generally applicable to somatic tissue obtained from the Pinus species including, but not limited to, the following: *Pinus taeda* (loblolly pine), *P. elliottii* (slash pine), *P. palustris* (longleaf pine), *P. serotina* (pond pine), *P. echinata* (shortleaf pine), *P. clausa* (sand pine), *P. glabra* (spruce pine), *P. rigida* (pitch pine), *P. echinata* (shortleaf pine), *P. nigra* (Austrian pine), *P. resinosa* (red pine), *P. sylvestris* (Scotch pine), *P. banksiana* (jack pine), *P. virginiana* (Virginia pine), *P. radiata* (Monterey pine), *P. contorta* (shore pine), *P. contorta latifolia* (lodgepole pine), *P. ponderosa* (ponderosa pine), *P. leiophylla* (Chihuahua pine), *P. jeffreyi* (Jeffrey pine), and *P. engelmannii* (Apache pine), *P. strobus* (eastern white pine), *P. monticola* (western white pine), and *P. lambertiana* (sugar pine), *P. albicaulis* (whitebark pine), *P. flexilis* (limber pine), *P. strobiformis* (southwestern white pine), *P. caribaea* (Caribbean pine), *P. patula* (Mexican weeping pine), *P. tecumumanii* (Tecun Uman pine), *P. maximinoi*, *P. oocarpa* (Ocote Pine) and *P. chiapensis* (Mexican White pine). In addition, the current invention is specifically applicable to interspecies hybrids of the above mentioned pines including *Pinus rigida×P. taeda, P. serotina×P. taeda*, and reciprocal crosses.

It is further preferred to utilize the present method with Southern yellow pines, *Pinus rigida,* and hybrids thereof. Those skilled in the art recognize that several species of pine indigenous to the Southeastern United States are closely related and hybridize naturally. Taxonomically this group of pines is referred to as "Southern yellow pines" and includes *Pinus taeda, P. serotina, P. palustris,* and *P. elliottii* (Preston 1989). In addition to the taxonomically similarity of the above Southern yellow pine species, these species have also responded similarly in studies on somatic embryogenesis attempts.

It is preferred that the additional phytohormone employed in the post-cryopreservation recovery medium be a member selected from the group consisting of auxins, cytokinins, and combinations thereof. Auxins suitable for use in the present invention include 2,4-D (2,4-dichlorophenoxy acetic acid), NAA (α-Naphthaleneacetic acid), and the like. It is preferred to incorporate a level of about 0.1 to 5.0 mg/l of auxin in the post-cryopreservation recovery medium. Cytokinins suitable for use in the present invention include, but are not limited to, the following: BAP ($N^6$-benzylamino-purine), kinetin (6-Furfurylaminopurine), zeatin (6-[4-hydroxy-3-methylbut-2-enylamino]purine), and combinations thereof. It is preferred to incorporate about 0.1 to 1.0 mg/l of cytokinin in the post-cryopreservation recovery medium. The above-noted levels and types of phytohormones (as well as the phytohormone ABA) are also suitable for use in the temporary recovery medium.

In addition to phytohormones, both the post-cryopreservation and temporary recovery media also require sufficient amounts of nutrients such as inorganic nutrients, vitamins, organic supplements, a carbon source (i.e., sugars), and the like to allow the thawed culture to recover from the cryogenic freezing process and cryopreservation. It is preferred to employ in the media a sugar selected from the group consisting of glucose, maltose, sucrose, and combinations thereof. The preferred amount of sugar is in the range of about 10.0 to 40.0 g/l. However, the present method is not limited to any single culture nutrient medium formulation. It should be understood that any nutrient media commonly used in conifer somatic embryogenesis will be suitable for use with this invention.

Additionally, both the post-cryopreservation recovery medium and the temporary recovery medium require a suitable level of gelling agent. It is preferred to incorporate a level of gelling agent selected from the group consisting of 6.0 to 9.0 g/l of agar, 1.75 to 4.0 g/l of gellan gum, 6.0 to 8.0 g/l of agarose, 3.5 to 5.0 g/l of AGARGEL, and combinations thereof into the recovery media.

The procedures for thawing cryopreserved embryogenic cultures are well-known to skilled artisans. It is preferred that the cryopreserved embryogenic cultures be thawed until ice crystals are no longer present in the cultures. It is further preferred that cryopreserved embryogenic cultures be thawed rapidly by placing the contained cultures in a warm (about 44° C.) water bath until the ice crystals have melted.

The preferred period of time for culturing the thawed embryogenic cultures on the post-cryopreservation medium is from about 1 to about 10 weeks. It is further preferred that the thawed embryogenic cultures be subcultured (i.e., transferred to the same, fresh, post-cryopreservation medium) at intervals of from about 1 day to about 3 weeks.

Where a temporary recovery medium is employed, it is preferred to culture the thawed embryogenic culture on the temporary recovery medium for a period of time sufficient to allow the concentration of cryoprotective chemicals and osmotic agents present in the embryogenic culture to be lowered via diffusion into the temporary recovery medium. The period of time commonly employed for such diffusion is from about 1 to about 72 hours; with the preferred period of time being from about 12 to about 48 hours.

A number of terms are known to have differing meanings when used in the literature. The following definitions are believed to be the ones most generally used in the field of plant biotechnology and are consistent with the usage of the terms in the present specification.

A "cell line" is a culture that arises from an individual explant.

"Clone" when used in the context of plant propagation refers to a collection of individuals having the same genetic makeup.

"Conversion" refers to the acclimatization process that in vitro derived germinating somatic embryos undergo in order to survive under ex vitro (nonaxenic) conditions, and subsequent continued growth under ex vitro conditions.

An "embryogenic culture" is a plant cell or tissue culture capable of forming somatic embryos and regenerating plants via somatic embryogenesis.

"Embryogenic tissue", in conifers, is a mass of tissue and cells comprised of very early stage somatic embryos and suspensor-like cells embedded in a mucilaginous matrix. This has also been referred to as "embryogenic suspensor masses" by some researchers and is also called "embryogenic callus" in some of the conifer somatic embryogenesis literature; but most researchers believe it is not a true callus.

An "explant" is the organ, tissue, or cells derived from a plant and cultured in vitro for the purpose of starting a plant cell or tissue culture.

"Field planting" is the establishment of laboratory, greenhouse, nursery, or similarly grown planting stock under field conditions.

"Fresh weight" is the weight in grams of a sample of the fully-hydrated embryogenic culture.

"Genotype" is the genetic constitution of an organism; the sum total of the genetic information contained in the DNA of an organism.

"Germination" is the emergence of the radicle or root from the embryo.

"Initiation" is the initial cellular proliferation or morphogenic development that eventually results in the establishment of a culture from an explant.

"Megagametophyte" is haploid nutritive tissue of the conifer seed, of maternal origin, within which the conifer zygotic embryos develop.

"Nutrients" are the inorganic chemicals (e.g., nitrogen), vitamins, organic supplements, carbon sources, and the like which are necessary for the nourishment of the cultures (resulting in their growth differentiation and/or regeneration).

"Phytohormones" are chemical substances, either naturally occurring or synthesized compounds, which affect the growth, differentiation and development of plant cells, tissues and organs. Phytohormones are frequently applied exogenously to in vitro plant cells, tissues, and organs to achieve desired effects on growth and regeneration.

"Regeneration", in plant tissue culture, is a morphogenic response to a stimuli that results in the production of organs, embryos, or whole plants.

"Somatic embryogenesis" is the process of initiation and development of embryos in vitro from somatic cells and tissues.

A "somatic embryo" is an embryo formed in vitro from vegetative (somatic) cells by mitotic division of cells. Early stage somatic embryos are morphologically similar to immature zygotic embryos; a region of small embryonal cells subtended by elongated suspensor cells. The embryonal cells develop into the mature somatic embryo.

A "suspension culture" is a culture composed of cells and early stage somatic embryos suspended in a liquid medium, usually agitated on a gyratory shaker. An embryogenic suspension culture in conifers is usually composed of early stage somatic embryos with well-formed suspensor cells and dense cytoplasmic head cells that float freely in the liquid medium.

The following examples are provided to further illustrate the present invention and are not to be construed as limiting the invention in any manner.

EXAMPLE 1

Immature seed cones were collected from six different loblolly pine (*Pinus taeda*) line sources (A1, A2, A3, A4, A5 and A6) located in Westvaco's South Carolina coastal breeding orchards near Charleston, S.C. The seed cones were collected when the dominant zygotic embryo was at the precotyledonary stage of development. Using the classification system of Hakman and von Arnold (1988), the dominant zygotic embryo at this stage is referred to as being at stage 2; that is, an embryo with a prominent embryonic region with a smooth and glossy surface, subtended by elongated suspensor cells which are highly vacuolated. Embryos which have progressed further in their development (to stage 3) will have cotyledon primordia, and will not be at an optimum stage of development for culture initiation. Although zygotic embryos at an earlier stage of development (stage 1) were also used effectively to initiate embryogenic cultures, stage 2 embryos were optimum (and therefore preferred). The stage of zygotic embryo development was checked by extracting megagametophytes from seeds, longitudinally dissecting megagametophytes, and removing zygotic embryos for examination. This extraction and examination of the zygotic embryos was done under a dissection microscope. Loblolly pine cones collected from breeding orchards in the Charleston, S.C. area reach the desired precotyledonary stage of development (stage 2) in mid to late July. Based on the finding that fertilization in loblolly pine occurred in mid June, the optimum stage corresponded to about 4 to 6 weeks post-fertilization.

Seed cones were harvested from selected trees, placed in plastic bags and stored at 4° C. until used for culture initiation. If the cones were stored for more than two weeks at 4° C., they were aired and dried out weekly (placed at 23° C., ambient laboratory conditions for 2–3 hours) to prevent growth of fungi on the surface of the cones and concomitant deterioration of seed quality.

For culture initiation intact seeds removed from seed cones were surface sterilized by treatment in a 10 to 20% commercial bleach solution (equivalent of a 0.525% to 1.050% sodium hypochlorite solution) for 15 minutes followed by three sterile water rinses (each of five minutes duration). Seeds were continuously stirred during the sterilization and rinsing process.

Megagametophytes containing developing zygotic embryos were used as the explant for culture initiation. The seed coats of individual seeds were cracked open with the use of a sterile hemostat. The intact megagametophyte (which contains the developing zygotic embryos) was removed from the opened seed coat with forceps. Tissues attached to the megagametophyte, such as the megagametophyte membrane and the nucellus were removed from the megagametophyte and discarded. The megagametophyte was placed on culture medium (longitudinal axis of megagametophyte parallel to the surface of culture medium) with forceps. The micropyle end of the megagametophyte was placed in contact with (but not submerged in) the culture initiation medium.

The culture medium employed for initiation was the $DCR_1$ formulation shown in Table I below, with the modification that 1.0 to 2.0 g/l of GELRITE® (a gellan gum manufactured by Merck, Inc.) was employed. The pH of the medium was adjusted to 5.8 with KOH and HCl prior to autoclaving at 110 kPa (16 psi) and 121° C. for 20 minutes. Aqueous stock solutions of L-glutamine were filter sterilized and added to warm (about 60° C.) medium prior to pouring the medium into culture plates. Approximately 20 ml of medium was poured into 100×15 mm sterile plastic petri plates.

TABLE I

Formulation of $DCR_1$ culture medium.[a]

| COMPONENT | Concentration (mg/l) |
|---|---|
| $NH_4NO_3$ | 400.00 |
| $KNO_3$ | 340.00 |
| $Ca(NO_3)_2.4H_2O$ | 556.00 |
| $MgSO_4.7H_2O$ | 370.00 |
| $KH_2PO_4$ | 170.00 |
| $CaCl_2.2H_2O$ | 85.00 |
| KI | 0.83 |
| $H_3BO_3$ | 6.20 |
| $MnSO_4.H_2O$ | 22.30 |
| $ZnSO_4.7H_2O$ | 8.60 |
| $Na_2MoO_4.2H_2O$ | 0.25 |
| $CuSO_4.5H_2O$ | 0.25 |
| $CoCl_2.6H_2O$ | 0.03 |
| $NiCl_2.6H_2O$ | 0.03 |
| $FeSO_4.7H_2O$ | 27.80 |
| $Na_2EDTA$ | 37.30 |
| Nicotinic acid | 0.50 |
| Pyridoxine HCl | 0.50 |
| Thiamine HCl | 1.00 |
| Glycine | 2.00 |
| Auxin[b] | 3.00 |
| Cytokinin[c] | 0.50 |
| | Concentration (g/l) |
| Inositol | 0.50 |
| Casein hydrolysate | 0.50 |
| L-glutamine | 0.25 |
| Sucrose | 30.00 |
| GELRITE[d] | 2.00 |

[a]Modification of Gupta and Durzan (1985) DCR medium.
[b]2,4-dichlorophenoxyacetic acid (2,4-D).
[c]$N^6$-benzylaminopurine (BAP) [or $N^6$-benzyladenine (BA)].
[d]GELRITE ® (a gellan gum manufactured by Merck, Inc.).

After megagametophyte explants were placed in culture, the perimeter of the plate was sealed with two wraps of PARAFILM® (manufactured by American Can Co.). The plates were incubated in the dark at a constant temperature of 23° C. After about 7 to 21 days, embryogenic tissue extruded from the micropyle of the megagametophyte explants. After 28 days in culture embryogenic tissue was removed from responsive megagametophyte explants and moved to a new position on the same culture plate, or the embryogenic tissue was transferred to a new culture plate containing the same culture medium as used for initiation. Each individual culture derived from an individual megagametophyte explant was kept separate and assigned a cell line identification code.

Cultures were maintained on semi-solid $DCR_1$ medium by subculturing masses of embryogenic tissue every 14 to 21 days to fresh medium.

Each embryogenic culture was cryopreserved as follows. Embryogenic tissue (7 to 14 days since the last subculture) was dispersed in liquid $DCR_1$ medium (the $DCR_1$ medium of Table I without the GELRITE) which contained 0.4 molar sorbitol as described in U.S. Pat. No. 5,506,136. The amount of embryogenic tissue used was sufficient to result in a 40% suspension (i.e., 4 ml volume of embryogenic tissue added to 6 ml of liquid medium). An Erlenmeyer flask containing the suspension was incubated for 24 hours in the dark on a gyrotory shaker (100 rpm), and then placed on ice. Five aliquots of the cryoprotective chemical dimethyl sulfoxide (DMSO) were aseptically added to the suspension to bring the final concentration of DMSO to 10% (vol/vol). One milliliter aliquots of the suspension containing DMSO were then transferred to 2 ml NALGENE® cryogenic vials (manufactured by the Nalge Co.), placed in programmable freezer (Model 9000 manufactured by Gordinier Electronics) and cooled to −35° C. at a rate of 0.33° C. per minute. The cultures were cryopreserved by immersing the cryogenic vials in liquid nitrogen inside a cryogenic storage tank (Model #CY50945 manufactured by Thermolyne, Inc.). The cultures remained in cryogenic storage for at least 36 months prior to retrieval.

The cryogenic vials were retrieved from the cryogenic storage tank and placed in 44° C. water until the ice crystals in the frozen embryogenic cultures were melted. The thawed culture from each cryogenic vial was aseptically pipetted and dispensed onto a sterile 7 cm×7 cm NITEX nylon 35 µm pore size membrane (commercially available from Sefar, Inc.) which had been placed on top of two sterile filter papers (Whatman no. 2 commercially available from Whatman International Ltd.) to absorb excess liquid from the culture and membrane. Each nylon membrane containing embryogenic culture was then transferred to a $DCR_1$ medium which served as a temporary recovery medium for 24 hours in order to lower the concentration of cryoprotective chemicals and osmotic agents contained in the culture.

Each nylon membrane containing embryogenic tissue was then transferred to one of two post-cryopreservation medium treatments. One treatment was $DCR_1$ medium without ABA. The other treatment was $DCR_1$ medium with 30 mg/l of ABA. The initial fresh weight ($FW_0$) of the embryogenic tissue was measured aseptically at this time. There were 3 plates (each derived from an individual cryogenic vial) per treatment and cell line. The embryogenic cultures on membranes were transferred after 24 hours, and thereafter, every 14 days to a new plate of the same medium. The culture environment during post-cryopreservation recovery and growth was 23° C. in the dark. At 25 days after retrieval from cryogenic storage the final fresh weight ($FW_F$) of the proliferating embryogenic culture was measured. The growth of the embryogenic tissue during the post-cryopreservation treatments was calculated as a percent increase in fresh weight relative to the initial fresh weight as follows: $((FW_F-FW_0)/FW_0)*100$. The results are shown in Table II below.

EXAMPLE 2

Immature seed cones were collected from four different loblolly pine (*Pinus taeda*) line sources (B1, B2, B3, and B4) located in Westvaco's S.C. coastal breeding orchards near Charleston, S.C. These seed cones were employed to initiate embryogenic cultures via the procedure described in Example 1.

Newly initiated embryogenic tissue, which extruded from the micopyle of the megagametophyte explants, was transferred from the initiation medium to the $DCR_1$ medium listed in Table I. While on maintenance medium, the cultures were subcultured at three-week intervals by plating the newly formed, mucilaginous tissue on to fresh medium. Suspension cultures of each cell line were established by inoculating a 125 ml NEPHELO® sidearm flask (manufactured by Kontes Chemistry and Life Sciences Products) with 500 mg of embryogenic tissues, and then adding 10 ml of sterilized liquid $DCR_1$ medium. The liquid $DCR_1$ medium was composed of the $DCR_1$ listed in Table I, less the GELRITE and with the addition of 0.5 g/l of activated carbon.

The flasks containing the cells in liquid medium were then placed on a gyrotory shaker at 100 rpm in the dark at 23° C. One day following placement in the liquid medium, cells and medium were decanted into the sidearm portion of the flasks and allowed to settle for 30 minutes, after which time the settled cell volume (SCV) was recorded in millimeters for each flask by placing a ruler next to the sidearm. This measurement was made one day after initiation in order to allow air bubbles in the tissue clumps to disperse to enable the tissues to settle. At 7-day intervals the cell growth was measured in the sidearm by allowing the cells to settle for 30 minutes and then measuring the settled cell volume (SCV). When the SCV doubled from the original starting SCV, the liquid in each flask was brought up to 20 mls with the same fresh medium as used to establish the suspension culture. When the SCV doubled again a flask was split 1:1 with a 125 ml non sidearm flask containing 20 mls of the same fresh medium. This subculturing method, termed splitting, involved pouring 20 mls of fresh medium into the old culture flask, swirling to evenly distribute the cells, and pipetting 20 mls of the resulting 40-ml culture into a non-sidearm flask. At each 7-day interval the SCV was determined and the flasks were split when the SCV was greater than or equal to twice the starting SCV. After about 2 weeks the cultures in the liquid medium began to show obvious signs of growth and in about 4–6 weeks the cultures stabilized to the point where they needed to be subcultured every 7 to 14 days. While the cultures could be maintained in 20 mls in 125 ml sidearm flasks, they were instead transferred to 250 ml sidearm flasks containing 40 mls of medium for routine maintenance. When the SCV doubled in the 125 ml sidearm, the entire contents of the 125 ml flask were transferred to a 250 ml sidearm and an additional 20 mls of fresh medium was added to give a total volume of 40 mls of medium.

Each cell line was cryopreserved as follows. The liquid suspension cultures (7 days since the last subculture) were aseptically centrifuged at 1500 rpm for 10 minutes (400 g-force) to separate the embryogenic tissue from the liquid medium. The supernatant medium was removed from the embryogenic tissue. To the remaining volume of centrifuged embryogenic tissue, was added an equal volume of liquid $DCR_1$ medium containing 0.8 molar sorbitol, so that the final sorbitol concentration was 0.4 molar. An Erlenmeyer flasks containing each suspension was incubated for 24 hours in the dark on a gyrotory shaker (100 rpm), and then placed on ice. The cryoprotective chemical DMSO was added to the chilled cultures at one time to bring the final concentration of DMSO to 10% (vol/vol). The suspension containing DMSO was transferred to cryogenic vials, placed in the programmable freezer, cooled to −35° C. at 1° C. per minute, and cryopreserved as described in Example 1. The cultures remained in cryogenic storage for 8 months prior to retrieval.

The cryogenic vials were retrieved from the cryogenic storage tank, thawed and transferred to temporary recovery medium and post-cryopreservation medium treatments (which contained no ABA or 30 mg/l of ABA) as previously described in Example 1. There were 5 plates (each from individual cryogenic vials) per treatment and cell line. At 26 days after retrieval from cryogenic storage the final fresh weight of the proliferating embryogenic culture was measured and growth calculated as in Example 1. The data were analyzed statistically by cell line using single-factor analysis of variance, and results are summarized in Table II below.

TABLE II

Percent Increase in Fresh Weight of Pine Embryogenic Cell Lines Retrieved from Cryopreservation on Post-Cryopreservation Recovery Medium

| Cell Line | Average Percent Increase in Fresh Weight | | Additional Culture Growth on | Probability[3] |
|---|---|---|---|---|
| | $DCR_1 - ABA$[1] | $DCR_1 + ABA$[2] | $DCR_1 + ABA$ | |
| A1 | 134 | 270 | yes | 0.34 |
| A2 | 5370 | 7484 | yes | 0.02* |
| A3 | 427 | 4065 | yes | <0.001* |
| A4 | 1582 | 1652 | yes | 0.95 |
| A5 | 3701 | 6479 | yes | 0.001* |
| A6 | 609 | 1221 | yes | 0.36 |
| B1 | 425 | 195 | no | 0.16 |
| B2 | 22 | 29 | yes | 0.77 |
| B3 | 2216 | 3259 | yes | 0.01* |
| B4 | 31 | 34 | yes | 0.69 |
| Average: | 1452 | 2469 | yes | |
| Increase: | — | 70% | yes | |

[1]The designation "− ABA" means that the medium did not contain ABA.
[2]The designation "+ ABA" means that the medium contained 30 mg/l ABA.
[3]An asterisk indicates a statistically higher percent increase on the + ABA treatment (probability $\leq$ 0.05).

The addition of ABA to the post-cryopreservation medium improved growth of pine embryogenic tissue retrieved from cryogenic storage. Nine of the ten cell lines tested in the two experiments had higher percent increases in fresh weight of embryogenic tissue on the treatment with ABA added to the post-cryopreservation medium. Since the ten cell lines were derived from seven genetically different families of loblolly pine, the results suggest that inclusion of ABA in the post-cryopreservation medium is beneficial with most cell line genotypes. The overall average percent increase in fresh weight of all ten cell lines was 70% higher on the post-cryogenic medium treatment with ABA compared to the medium without ABA.

These results are important, since it is critical to obtain as much embryogenic tissue growth as possible, in the shortest period of time, when retrieving cultures from cryopreservation. It is well known the regeneration potential of embryogenic cell lines, and in particular, embryogenic cell lines of pine species, declines with increasing time in culture. Therefore, any improvement that increases embryogenic tissue proliferation is important for both large scale-production of clonal planting stock or for use of somatic embryogenesis in conjunction with genetic engineering methods.

The effect of ABA on the post-cryogenic growth depended on the cell line. In some cell lines, A3, A5 and B3, the medium with ABA resulted in highly statistically significant increase in fresh weight. For example, cell line A3 produced a total fresh weight of 5.17 grams of embryogenic tissue from three cryogenic vials grown on medium with ABA, versus 1.07 grams on medium without ABA. The lack of a statistically significant treatment effect in some cell lines may in part be due to the wide variation in growth among plates within a treatment. Further research is needed to understand factors causing this variation in growth among cultures from different cryogenic vials of the same cell line retrieved from cryopreservation. In practice, several cryogenic vials of each cell line are typically retrieved from cryogenic storage simultaneously, and it is the total amount of tissue harvested from all vials that is important for subsequent use in clonal propagation or genetic engineering.

Thus, the examples show that it is generally beneficial to include ABA in the post-cryopreservation medium, and that it significantly increases growth in some pine cell lines.

EXAMPLE 3

Five different pine embryogenic cell lines chosen at random from a long-term cryogenic storage bank were initiated, grown as liquid embryogenic suspension cultures, and cryopreserved via the methods described in Examples 1 and 2. The five cell lines included: one pitch×loblolly pine interspecies hybrid cell line (AA-24) and four loblolly pine cell lines (G-05, K-12, E-117 and O-72). Also, two additional pitch×loblolly pine $F_1$ hybrid cell lines (Q-01 and Q-39) were initiated, grown as liquid embryogenic suspension cultures, and cryopreserved via the methods described in Examples 1 and 2 except that the initiation and maintenance media contained 10.0 mg/l of ABA (as taught in U.S. Pat. No. 5,856,191). The seven cell lines were retrieved from cryogenic storage, thawed, and transferred, via the procedure described in Example 2. Each cell line was subjected to three post-cryopreservation medium treatments. The first treatment was a control (i.e., $DCR_1$ medium without ABA), the second treatment was $DCR_1$ medium with 10 mg/l of ABA, and the third treatment was $DCR_1$ medium with 30 mg/l of ABA. There were four plates (each derived from an individual cryogenic vial) per treatment and cell line.

The embryogenic cultures on membranes were transferred after 24 hours from the temporary recovery medium onto the post-cryopreservation medium and thereafter, every 14 days to a new plate of the same post-cryopreservation medium. The culture environment during post-cryopreservation recovery and growth was 23° C. in the dark. At 28 days after retrieval from cryogenic storage the final fresh weight of the proliferating embryogenic culture was measured. The data were analyzed using the SAS GLM ANOVA statistical software program (Release 6.12 commercially available from the SAS Institute, Inc.), and the results are shown in Table III below.

TABLE III

Embryogenic Cultures Retrieved from Cryopreservation on Post-Cryopreservation Recovery Medium

| | Mean Culture Fresh Weight (g) | | |
|---|---|---|---|
| Cell Culture Line | No ABA | 10 mg/l ABA | 30 mg/l ABA |
| AA-24 | 4.85 | 5.22 | 5.45[a] |
| G-05 | 2.52 | 3.82[a] | 3.73 |
| K-12 | 0.87 | 0.55 | 1.09[a] |
| E-117 | 0.05 | 0.38[a] | 0.33 |
| O-72 | 0.07 | 0.09 | 0.10[a] |
| Q-01 | 1.18 | 2.91[b] | 3.81[ab] |
| Q-39 | 0.11 | 0.01 | 0.17 |
| Average: | 1.38 | 1.86 | 2.10[a] |
| % Increase: | control | 35% | 52%[a] |

[a]Treatment with the highest fresh weight.
[b]Means within cell line different according to Duncan's multiple range test (alpha = 0.05).

The statistical analysis showed that there was a significant cell line by ABA level interaction (p=0.0001). Thus the effect on growth of adding ABA to the post-cryogenic recovery medium depended on the particular cell line tested. Overall, the addition of ABA to the post-cryopreservation recovery medium improved the average growth of all of the cultures retrieved from cryogenic storage by 35 to 52% (Table III). All seven of the cell lines tested grew better on either the 10 mg/l or 30 mg/l ABA treatment, when compared to control treatments which did not contain any ABA. Two cell lines (G-05 and E-117) grew best on post-cryogenic recovery medium with 10 mg/l ABA, whereas the other five cell lines tested grew best on the 30 mg/l level. The lack of statistical significance among most treatments within individual cell lines appeared to be related to variability in growth between replicate samples. For example, even though the mean values for the fresh weight of the 10 mg/l and 30 mg/l ABA treatments of cell line G-05 were 52% and 48% higher, respectively, than the control treatment which did not contain ABA, the differences among the treatments for this specific cell line were not statistically significant. However, multiple cryogenic vials are typically retrieved from cryogenic storage, at one time, for an individual cell line. It is, therefore, the total amount of tissue accumulated from the combined multiple plates retrieved from cryogenic storage that is important for its subsequent use in the somatic embryogenic regeneration process. The results noted in Table III above show that the addition of ABA to the post-cryogenic recovery medium improved the growth of cryopreserved embryogenic cultures with both loblolly pine and pitch by loblolly pine interspecies hybrid cell lines. Furthermore, the results obtained for cell lines Q-01 and Q-39 show that it is advantageous to employ ABA in both the initiation and maintenance phase prior to cryopreservation (as taught in U.S. Pat. No. 5,856,191), and in the post-cryopreservation phase of culture growth and recovery from cryogenic storage as taught in the current invention.

In summary, the results of this experiment showed that more rapid growth is obtained when cultures are grown on post-cryogenic recovery medium containing 10.0 or 30.0 mg/l ABA, as compared to medium without ABA, although the degree of improvement is dependent on the particular cell line.

EXAMPLE 4

The purpose of this experiment was to determine whether addition of ABA to the post-cryopreservation culture medium improved the yield of somatic embryos harvested from the cultures after they were retrieved from cryogenic storage. The six loblolly pine cell lines retrieved from cryogenic storage in Example 1 were used in this experiment. Embryogenic tissue from each cell line was dispersed onto nylon membranes using liquid $DCR_1$ medium (formulation in Table 1 without the GELRITE). Four ml of embryogenic culture retrieved from cryogenic storage of each cell line and treatment (both the no ABA and the 30 mg/l ABA post-cryopreservation recovery medium) was added to 5 ml of liquid $DCR_1$ medium and dispersed by agitation. One ml aliquots of the suspension were dispensed using a sterile 5-ml pipette with a cotton plug. Each 1 ml aliquot was transferred to the surface of a sterile 4 cm nylon membrane positioned on top of two sterile Whatman No. 2 filter papers in the bottom of an empty 15×100 mm sterile plastic culture plate. The nylon membranes with the dispersed embryogenic cultures were placed on either $DCR_1$ medium containing 30 mg/l ABA or the same medium without any ABA depending on their respective post-cryopreservation recovery medium treatments from which they were derived. This resulted in 3 plates per treatment, with each plate containing 3 nylon membranes with 1 ml of cells on each membrane. The tissue on the nylon membranes was cultured for 5–6 days at 23° C. in the dark to induce proliferation from the newly dispersed cultures. The nylon membranes with tissue were then transferred to an embryo development medium (see Table IV below) as described in U.S. Pat. No. 5,731,204 (Rutter et al.), to test the yield of stage 3 cotyledonary somatic embryos. The plates with membranes containing the embryogenic cultures were incubated in the dark at 23° C. The nylon membranes with the embryogenic cultures were transferred to new plates containing the same fresh embryo development medium every three weeks. After a total of nine weeks, the number of stage 3 embryos was counted on each membrane, and the data were analyzed using SAS GLM ANOVA statistical software. The results are shown in Table V below.

TABLE IV

Formulations Of Embryo Development Medium

| COMPONENT | Concentration (mg/l) |
| --- | --- |
| $KNO_3$ | 100.00 |
| $MgSO_4.7H_2O$ | 370.00 |
| $KH_2PO_4$ | 170.00 |
| $CaCl_2.2H_2O$ | 440.00 |
| KCl | 745.00 |
| KI | 0.83 |
| $H_3BO_3$ | 6.20 |
| $MnSO_4.H_2O$ | 16.90 |
| $ZnSO_4.7H_2O$ | 8.60 |
| $Na_2MoO_4 2H_2O$ | 0.25 |
| $CuSO_4.5H_2O$ | 0.03 |
| $CoCl_2.6H_2O$ | 0.03 |
| $FeSO_4.7H_2O$ | 27.80 |
| $Na_2EDTA$ | 37.30 |
| Nicotinic acid | 0.50 |
| Pyridoxine HCl | 0.10 |
| Thiamine HCl | 0.10 |
| Inositol | 100.00 |
| L-glutamine | 14,500.00 |
| Maltose | 60,000.00 |
| Polyethylene Glycol (4,000 Mol. Wt.) | 60,000.00 |
| GELRITE | 2,000.00 |
| Abscisic acid | 125.00 |

TABLE V

Yield of Somatic Embryos From Embryogenic Cultures Retrieved From Cryopreservation on Post-cryopreservation Recovery Medium

| | Total Number of Somatic Embryos Harvested | | |
| --- | --- | --- | --- |
| Cell Line | No ABA | 30 mg/l ABA | Probability[1] |
| A1 | 36 | 404 | <0.001* |
| A2 | 40 | 82 | 0.03* |
| A3 | 0 | 0 | — |
| A4 | 6 | 43 | 0.001* |
| A5 | 0 | 15 | 0.02* |
| A6 | 54 | 44 | 0.43 |
| Total No. | 136 | 588 | |
| % Increase | Control | 332% | |

[1]An asterisk indicates a statistically higher mean number of embryos harvested from the 30 mg/l ABA treatment (probability ≦ 0.05).

The results of this experiment showed that with most cell lines higher numbers of embryos were obtained when cultures were recovered on post-cryogenic recovery medium containing 30.0 mg/l of ABA, as compared to medium without ABA, although the degree of improvement is dependent on the particular cell line. The total number of stage 3 somatic embryos harvested from the 6 cell lines recovered on the post-cryogenic recovery medium containing 30.0 mg/l of ABA was increased over three-fold (332%) when compared to the embryos harvested from recovery medium which did not contain ABA.

In summary, the results from the examples demonstrate that the addition of ABA to the post-cryogenic recovery medium improves both the culture growth and the subsequent somatic embryo production of most of the pine embryogenic cultures.

Many modifications and variations of the present invention will be apparent to one of ordinary skill in the art in light of the above teachings. It is therefore understood that the scope of the invention is not to be limited by the foregoing description, but rather is to be defined by the claims appended hereto.

BIBLIOGRAPHY

Becwar, M. R., E. E. Chesick, L. W. Handley, M. R. Rutter. Method for Regeneration of Coniferous Plants by Somatic Embryogenesis. U.S. Pat. No. 5,506,136—issued Apr. 9, 1996.

Benson, E. E., P. T. Lynch, and G. N. Stacey. Advances in Plant Cryopreservation Technology: Current Applications in Crop Plant Biotechnology. *CAB International*, 1998.

Gupta, P. K. and D. J. Durzan. Shoot Multiplication from Mature Trees of Douglas-fir (*Pseudotsuga menziesii*) and Sugar Pine (*Pinus lambertiana*). *Plant Cell Reports* 4:177–179, 1985.

Gupta, P. K. and G. S. Pullman. Method for Reproducing Coniferous Plants by Somatic Embryogenesis. U.S. Pat. No. 4,957,866—issued Sep. 18, 1990.

Gupta, P. K. and G. S. Pullman. Method for Reproducing Coniferous Plants by Somatic Embryogenesis Using Abscisic Acid and Osmotic Potential Variation. U.S. Pat. No. 5,036,007—issued Jul. 30, 1991.

Gupta, P. K. and G. S. Pullman. Method for Reproducing Coniferous Plants by Somatic Embryogenesis Using Stepwise Hormone Adjustment. U.S. Pat. No. 5,236,841—issued Aug. 17, 1993.

Hakman, I. and S. von Arnold. Plantlet Regeneration Through Somatic Embryogenesis in *Picea abies* (Norway spruce). *Journal of Plant Physiology* 121:149–158, 1985.

Hakman, I., L. C. Fowke, S. von Arnold, and T. Eriksson. The Development of Somatic Embryos in Tissue Cultures Initiated from Immature Embryos of *Picea abies* (Norway spruce). *Plant Science* 38:53–59, 1985.

Hakman, I. C. and S. von Arnold. Somatic Embryogenesis and Plant Regeneration from Suspension Cultures of *Picea glauca* (White spruce). *Physiologia Plantarum* 72:579–587, 1988.

Handley, L. W. and A. P. Godbey. Embryogenic Coniferous Liquid Suspension Cultures. U.S. Pat. No. 5,491,090—issued Feb. 13, 1996.

Handley, L. W. III. Method for Regeneration of Coniferous Plants by Somatic Embryogenesis in Culture Media Containing Abscisic Acid. U.S. Pat. No. 5,856,191. Issued Jan. 5, 1999.

Kendall, E. J., K. K. Kartha, J. A. Qureshi, P. Chermak. Cryopreservation of Immature Spring Wheat Zygotic Embryos Using an Abscisic Acid Pretreatment. Plant Cell Reports 12:89–94, 1993.

Luo, J. and B. M. Reed. Abscisic Acid-responsive Protein, Bovine Serum Albumin, and Proline Pretreatments Improve Recovery of in vitro Currant Shoot-tip Meristems and Callus Cryopreserved by Vitrification. Cryobiology 34:240–250, 1997.

Murashige, T. and F. Skoog. A Revised Medium for Rapid Growth and Bioassays with Tobacco Tissue Culture. Physiologia Plantarum 15:473–497, 1962.

Pullman, G. S. and P. K. Gupta. Method for Reproducing Coniferous Plants by Somatic Embryogenesis Using Adsorbent Materials in the Development Stage Media. U.S. Pat. No. 5,034,326—issued Jul. 23, 1991.

Pullman, G. S. and P. K. Gupta. Method for Reproducing Conifers by Somatic Embryogenesis Using Mixed Growth Hormones for Embryo Culture. U.S. Pat. No. 5,294,549—issued Mar. 15, 1994.

Roberts, D. R. Process for the Production, Desiccation and Germination of Conifer Somatic Embryos. U.S. Pat. No. 5,183,757—issued Feb. 2, 1993.

Rutter, M. R., L. W. Handley, and M. R. Becwar. Method for regeneration of coniferous plants by somatic embryogenesis employing polyethylene glycol. U.S. Pat. No. 5,731,191—issued Mar. 24, 1998.

Rutter, M. R., L. W. Handley, and M. R. Becwar. Method for Regeneration of Coniferous Plants by Somatic Embryogenesis Employing Polyethylene Glycol. U.S. Pat. No. 5,731,204—issued Mar. 24, 1998.

Uddin, M. Somatic Embryogenesis in Gymnosperms. U.S. Pat. No. 5,187,092—issued Feb. 16, 1993.

von Arnold, S. and I. Hakman. Regulation of Somatic Embryo Development in *Picea Abies* by Abscisic Acid (ABA). *Journal of Plant Physiology* 132:164–169, 1988.

What is claimed is:

1. A method for increasing the proliferative growth of embryogenic cultures of coniferous plants which have been subjected to cryopreservation comprising:
   (a) thawing the embryogenic culture; and
   (b) culturing the thawed embryogenic culture on post-cryopreservation recovery medium containing a sufficient amount of nutrients, a suitable level of gelling agent, abscisic acid, and a sufficient amount of additional phytohormone to increase the proliferative growth of the embryogenic culture.

2. A method for increasing the proliferative growth of embryogenic cultures of coniferous plants which have been subjected to cryopreservation comprising:
   (a) thawing the embryogenic culture,
   (b) culturing the thawed embryogenic culture on temporary recovery medium containing a sufficient amount of nutrients, a suitable level of gelling agent, and a sufficient amount of phytohormone for a period of time sufficient to lower the concentration of cryoprotective chemicals and osmotic agents contained in the embryogenic culture; and
   (c) further culturing the thawed embryogenic culture on post-cryopreservation recovery medium containing a sufficient amount of nutrients, a suitable level of gelling agent, abscisic acid, and a sufficient amount of additional phytohormone to increase the proliferative growth of the embryogenic culture.

3. The method of claim 1 wherein the coniferous plant is a member selected from the group consisting of the genus Pinus.

4. The method of claim 3 wherein the coniferous plant is a member selected from the group consisting of *Pinus taeda, Pinus serotina, Pinus palustris, Pinus elliottii, Pinus rigida*, and hybrids thereof.

5. The method of claim 1 wherein the post-cryopreservation recovery medium contains from about 1.0 to about 100.0 mg/l of abscisic acid.

6. The method of claim 5 wherein the post-cryopreservation recovery medium contains from about 5.0 to about 50.0 mg/l of abscisic acid.

7. The method of claim 1 wherein the additional phytohormone is a member selected from the group consisting of auxins, cytokinins, and combinations thereof.

8. The method of claim 7 wherein the auxin is a member selected from the group consisting of 2,4-D(2,4-dichlorophenoxy acetic acid), NAA (α-Naphthaleneacetic acid), and combinations thereof.

9. The method of claim 7 wherein the cytokinin is a member selected from the group consisting of BAP ($N^6$-benzylamino-purine), kinetin (6-Furfurylaminopurine), zeatin(6-[4-hydroxy-3-methylbut-2-enylamino]purine), and combinations thereof.

10. The method of claim 1 wherein the nutrient is a member selected from the group consisting of inorganic nutrients, vitamins, organic supplements, carbon sources, and combinations thereof.

11. The method of claim 10 wherein the carbon source is a member selected from the group consisting of glucose, maltose, sucrose, and combinations thereof.

12. The method of claim 1 wherein the gelling agent is a member selected from the group consisting of agar, gellan gum, agarose, AGARGEL, and combinations thereof.

13. The method of claim 1 wherein the thawed embryogenic culture is cultured on the post-cryopreservation medium for a period of from about 1 to about 10 weeks.

14. The method of claim 13 wherein the thawed embryogenic culture is subcultured on post-cryopreservation medium at intervals of from about 1 day to about 3 weeks.

15. The method of claim 2 wherein the phytohormone employed in step (b) is a member selected from the group consisting of auxins, cytokinins, and combinations thereof.

16. The method of claim 2 wherein the thawed embryogenic culture is cultured on the temporary recovery medium for a period of about 1 to about 72 hours.

17. The method of claim 1 wherein the embryogenic culture has been transformed to contain at least one transgene.

18. The method of claim 1 wherein the cultured thawed embryogenic culture is employed to regenerate plants via somatic embryogenesis.

19. The method of claim 18 wherein the cultured thawed embryogenic culture employed to regenerate plants via somatic embryogenesis exhibits increased yields of somatic embryos.

20. The method of claim 2 wherein the coniferous plant is a member selected from the group consisting of the genus Pinus.

21. The method of claim 20 wherein the coniferous plant is a member selected from the group consisting of *Pinus taeda, Pinus serotina, Pinus palustris, Pinus elliottii, Pinus rigida*, and hybrids thereof.

22. The method of claim 2 wherein the post-cryopreservation recovery medium contains from about 1.0 to about 100.0 mg/l of abscisic acid.

23. The method of claim 22 wherein the post-cryopreservation recovery medium contains from about 5.0 to about 50.0 mg/l of abscisic acid.

24. The method of claim 2 wherein the phytohormone is a member selected from the group consisting of auxins, cytokinins, and combinations thereof.

25. The method of claim 24 wherein the auxin is a member selected from the group consisting of 2,4-D (2,4-dichiorophenoxy acetic acid), NAA (α-Naphthaleneacetic acid), and combinations thereof.

26. The method of claim 24 wherein the cytokinin is a member selected from the group consisting of BAP ($N^6$-benzylamino-purine), kinetin (6-Furfurylaminopurine), zeatin (6-[4-hydroxy-3-methylbut-2-enylamino]purine), and combinations thereof.

27. The method of claim 2 wherein the nutrient is a member selected from the group consisting of inorganic nutrients, vitamins, organic supplements, carbon sources, and combinations thereof.

28. The method of claim 27 wherein the carbon source is a member selected from the group consisting of glucose, maltose, sucrose, and combinations thereof.

29. The method of claim 2 wherein the gelling agent is a member selected from the group consisting of agar, gellan gum, agarose, AGARGEL, and combinations thereof.

30. The method of claim 2 wherein the thawed embryo genic culture is cultured on the post-cryopreservation medium for a period of from about 1 to about 10 weeks.

31. The method of claim 30 wherein the thawed embryogenic culture is subcultured on post-cryopreservation medium at intervals of from about 1 day to about 3 weeks.

32. The method of claim 2 wherein the embryogenic culture has been transformed to contain at least one transgene.

33. The method of claim 2 wherein the post-cryopreservation recovery medium embryogenic culture is employed to regenerate plants via somatic embryogenesis.

34. The method of claim 33 wherein the post-cryopreservation recovery medium embryogenic culture employed to regenerate plants via somatic embryogenesis exhibits increased yields of somatic embryos.

* * * * *